United States Patent
Nakamura

(10) Patent No.: US 9,335,567 B2
(45) Date of Patent: May 10, 2016

(54) METHOD FOR MANUFACTURING BINOCULAR LOUPE

(71) Applicant: Shoichi Nakamura, Nagano (JP)

(72) Inventor: Shoichi Nakamura, Nagano (JP)

(73) Assignees: ACP JAPAN; CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 284 days.

(21) Appl. No.: 14/245,435

(22) Filed: Apr. 4, 2014

(65) Prior Publication Data
US 2015/0286076 A1    Oct. 8, 2015

(51) Int. Cl.
| | | |
|---|---|---|
| A61B 3/10 | (2006.01) | |
| G02B 25/00 | (2006.01) | |
| G02C 13/00 | (2006.01) | |
| A61B 3/11 | (2006.01) | |
| G02C 7/08 | (2006.01) | |

(52) U.S. Cl.
CPC .............. G02C 13/005 (2013.01); A61B 3/111 (2013.01); G02B 25/004 (2013.01); G02C 7/088 (2013.01)

(58) Field of Classification Search
CPC .... G02B 25/004; G02B 25/02; G02B 25/001; G02B 7/002; G02B 7/102; G02B 7/12; G02B 23/18; G02B 3/14; G02B 21/02; G02B 21/22; G02C 7/088; G02C 11/04; G02C 13/005; G02C 3/02; G02C 9/00; G02C 9/02; G02C 9/04; A61B 3/102; A61B 3/111; A61B 1/00147; A61B 1/00188; A61B 1/0692; G01C 11/00
USPC .............. 351/57, 158, 159.01, 201, 204, 205, 351/232, 240, 246; 359/368, 375, 407, 409, 359/411, 419, 480, 481, 793, 811
See application file for complete search history.

(56) References Cited

U.S. PATENT DOCUMENTS

| | | | | |
|---|---|---|---|---|
| 2009/0231699 | A1* | 9/2009 | Nakamura ............. | G02B 7/002 359/481 |
| 2010/0290115 | A1* | 11/2010 | Chang .................... | G02C 7/088 359/481 |

FOREIGN PATENT DOCUMENTS

JP    2000-014639 A    1/2000

* cited by examiner

*Primary Examiner* — Bumsuk Won
*Assistant Examiner* — Collin X Beatty
(74) *Attorney, Agent, or Firm* — Manabu Kanesaka

(57) ABSTRACT

Provided is a method for manufacturing a binocular loupe, the method including radiating strobe light from a below-located operational manipulating position in a state that the operator wearing the frame on which the carrier lenses are mounted stares the operational manipulating position in a working posture to use the binocular loupe, photographing reflection light of the strobe light reflected from pupils of the operator with a camera 11, specifying pupil positions based on the image data, and determining downward wearing angles r1, r2 of the loupe units which are to be attached to the right and left carrier lenses based on distance A from the operational manipulating position P to the carrier lenses and a horizontal distance B from the operational manipulating position P to a vertical line passing through the carrier lens.

30 Claims, 12 Drawing Sheets

METHOD FOR MANUFACTURING BINOCULAR LOUPE

BACKGROUND OF THE INVENTION

1. Field of the Invention

The present invention relates to a binocular loupe which is used during medical surgery or precision machine operation, and in particular, relates to a method for manufacturing a binocular loupe in which loupe units are attached to carrier lenses in a frame.

2. Description of Related Arts

Conventionally, binocular loupes have been widely used as means to stare a target locally at hand in an enlarged manner in a variety of fields such as medical fields, precision machining, jewel processing, and the like. In such fields, it is required to be capable of staring with a high degree of accuracy.

As illustrated in FIG. 1, a binocular loupe 10 being a general lens fitting type is configured to include a frame 1 having the same structure as glasses to correct eyesight of an operator, loupe units 2 being a binocular loupe main body for enlarging an image of an operational target, carrier lenses 5 to which the loupe units 2 are attached as being fitted to the frame 1, attaching portions 3 for attaching the loupe units 2 to the carrier lenses 5, and frame temples 6 to be worn on the face of the operator. The loupe units 2 are inserted to opening portions which are formed at the carrier lenses 5 by performing cutting at the surface and is fixed with the attaching portions 3.

FIG. 2 is an explanatory view illustrating a state that the operator wears the binocular loupe 10. Similarly to normal grasses, the binocular loupe 10 can be worn to the face section with the frame temple portions 6 of the frame 1 hooked on the ears of the operator.

When the binocular loupe 10 having the above configuration is used especially in a medical field, the binocular loupe 10 is required to be matched to an inter-pupil distance and a working posture of each operator as being fatal to humans. In order to ensure a high degree of visibility, manufacturing is performed according to the following procedure in accordance with physicality of the operator.

(1) Selecting Frame Fitted to Physicality of Operator's Face

Here, the frame temple portions 6 fit to temporal regions of the head of the operator and curved leading end portions of the frame temple portions 6 appropriately hang on the ears. A nose pad which is arranged between a pair of the carrier lenses 5 is perfectly contacted to the glabella of the operator.

(2) Measuring Inter-Pupil Distance with PD Meter

In general, an inter-pupil distance is measured using a PD meter (for example, see Patent Literature 1). A viewing port for a measurer is arranged at one end of the PD meter and a window through which a subject sees the inside of a body is arranged at the other end thereof. The subject brings his/her eyes close to the window to stare a mark appearing in the body. When the measurer causes the right and left pupils of the subject to be matched by performing necessary operation during viewing through the viewing port, the PD meter optically reads out the image at that time. Then, the PD meter measures the inter-pupil distance and distances from the nose center to the centers of the right and left pupils of the subject and displays the result. At that time, the PD meter performs the measurement based on a previously-determined focal distance being 40 cm, for example. FIG. 3 illustrates an example of a measurement result performed with the PD meter. In FIG. 3, a numeral value at the left side denotes a distance from the nose center to the pupil center of the right eye of the subject, a numeral value at the right side denotes a distance from the nose center to the pupil center of the left eye of the subject, and a numeral value at the center denotes a distance between pupils of both eyes.

Meanwhile, a posture when an operator (a doctor) performs operation (a posture during surgery) looks as illustrated in FIG. 4 as the operator being in a state of staring a leading end of holding equipment (an operational manipulating position P). Although loupe units 2 are eliminated from a frame worn by the operator in FIG. 4, the operator observes the operational manipulating position P through loupe units 2 in an enlarged manner. Accordingly, for attaching the loupe units 2 to the frame 1, the loupe units 2 are not supposed to be attached as being perpendicular to a surface of the carrier lenses 5 of the frame 1. Here, it is required that the loupe units 2 are inclined downward (toward a lower frame edge side) as illustrated in FIG. 2 in the vertical direction and are inclined inward (toward a nose pad side) as illustrated in FIG. 5 in the horizontal direction.

Angles at which the right and left loupe units 2 are inclined inward are derived from the measurement result of the inter-pupil distance with the PD meter. According to the measurement result of FIG. 3, the distance from the center line L at the nose center to the center of the pupil of the right eye is 31 mm and the distance therefrom to the center of the pupil of the left eye is 29.5. Further, the measurement was performed with the focal distance set to 40 cm. Thus, inward wearing angles p, q being inward attaching angles of the right and left loupe units 2 to be attached to the surfaces of the right and left carrier lenses 5 are detected, respectively.

(3) Measuring Distance from Eyes to Operational Manipulating Position

The operator wearing the frame 1 without the loupe units 2 attached takes a working posture as illustrated in FIG. 4. In this state, a distance from eyes to the operational manipulating position P is measured by measuring a distance from the operational manipulating position P to a connecting part of the frame temple portion 6 and the frame 1.

FIG. 6 schematically illustrates measurement of the distance. Here, a distance A from the operational manipulating position P to the carrier lens 5 and a horizontal distance B from the operational manipulating position P to the vertical line passing through the carrier lens 5 in the horizontal direction as being perpendicular thereto are actually measured using a scale in a state that the operator wears the frame 1 and takes a posture to perform surgery. Then, an angle a sandwiched thereby is obtained from the actually-measured distances A, B.

Meanwhile, when the operator takes a posture to perform surgery, the frame 1 is forwardly leant owing to forward-leaning of the head of the operator (FIG. 4). The forward-leaning angle s is about 25 degrees with surgery in a standing posture such as surgical operation and is about 20 degrees with surgery in a sitting posture such as dental operation. Accordingly, downward wearing angle r1, r2 being downward angles at which the right and left loupe units 2 are attached to the carrier lenses 5 are obtained from the angle a and the forward-leaning angle s being 25 degrees or 20 degrees corresponding to surgery at which the binocular loupe 10 to be manufactured is to be used.

(4) Manufacturing Binocular Loupe

After the inward wearing angles p, q and the downward wearing angle r1, r2 are determined, opening portions are formed at the right and left carrier lenses 5 respectively at attaching positions of the loupe units 2 which are determined from the right and left pupil positions obtained through measurement of the inter-pupil distance. Then, the loupe units 2 are fitted to the opening portions while keeping the inward wearing angles p, q and the downward wearing angles r1, r2, so that the binocular loupe 10 is manufactured.

CITED LITERATURE

Patent Literature

Patent Literature 1: Japanese Patent Laid-Open No. 2000-14639

SUMMARY OF THE INVENTION

According to the abovementioned method for manufacturing a binocular loupe which has been used conventionally, the PD meter is used for measuring the inter-pupil distance. Here, the measurement has to be performed as selecting a focal distance among focal distances previously set in the PD meter. Accordingly, there may be a case that the selected focal distance is not matched to a distance from the eyes of an operator in the working posture thereof to the operational manipulating position P.

In addition, the PD meter is required to be used under conditions that measurement is performed during a staring direction of an object is horizontal. However, an operator performs operation in a state of staring downward in medical surgery. Accordingly, a measurement result of the PD meter causes errors against an inter-pupil distance in a surgery posture. Therefore, a conventional binocular loupe for operation in a downward posture has been insufficient from a viewpoint of accuracy.

In view of the abovementioned problems of the related art, the present invention provides a method for manufacturing a binocular loupe capable of providing an enlarged range of view matched to each operator by specifying accurate pupil positions and attaching angles of loupe units against surfaces of carrier lenses in accordance with a posture of the operator.

According to the present invention, a method for manufacturing a binocular loupe in which loupe units are attached to carrier lenses mounted on a frame selected in accordance with an operator includes steps of (a) radiating strobe light from a below-located operational manipulating position in a state that the operator wearing the frame on which the carrier lenses are mounted stares the operational manipulating position in a working posture to use the binocular loupe, (b) photographing reflection light of the strobe light reflected from pupils of the operator with a first imaging device which is arranged at the operational manipulating position, (c) obtaining side posture image data of the operator in the working posture with a second imaging device which is arranged at either or both of the right and left sides of the operator at a position or positions being apart therefrom by a predetermined distance, (d) electrically specifying a right pupil position (X1, Y1) and a left pupil position (X2, Y2) of the operator from a center point of the frame based on front image data obtained by the first imaging device, (e) measuring, from the side posture image data, a distance A from the operational manipulating position to the carrier lenses and a horizontal distance B from the operational manipulating position to a vertical line passing through the carrier lens in a direction perpendicular thereto, and determining downward wearing angles r1, r2 of the loupe units which are to be attached to the right and left carrier lenses based on the measured distance A and distance B, (f) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position, and (g) forming opening portions at the right and left carrier lenses based on the right pupil position, the left pupil position, the downward wearing angles r1, r2, and the inward wearing angles p, q, and inserting and fixing the right and left loupe units to the opening portions.

Here, the carrier lenses may be eyesight correcting lenses for the operator. Then, the carrier lenses may be manufactured, in a state that the operator is in a standing posture as looking into distance above the operational manipulating position after releasing the working posture, with steps of radiating strobe light from the operational manipulating position in a state that the operator wearing the frame on which the carrier lenses are mounted uses the binocular loupe in the standing posture, photographing reflection light of the strobe light reflected from pupils of the operator with the first imaging device which is arranged at the operational manipulating position, electrically specifying a right pupil position (X3, Y3) and a left pupil position (X4, Y4) of the operator from a center point of the frame based on front image data obtained by the first imaging device, and arranging centers of the eyesight correcting lenses at the right pupil position (X3, Y3) and the left pupil position (X4, Y4) of the operator.

Further, the loupe units may have fixed magnification power to provide enlarged view of the operational manipulating position or a zooming function with variable magnification power within a predetermined range.

Further, the first imaging device may be a digital camera which includes a strobe light radiation device and electrically stores image data in memory.

Further, the side posture image data of the operator may be obtained in the step (c) at timing as being synchronized with the strobe light radiating in the step (a).

Further, the step of electronically specifying the right pupil position (X1, Y1) and the left pupil position (X2, Y2) of the operator in the step (d) may be performed by determining center points of segments, in predetermined sections of the front image data at right and left sides from the center point of the frame, which have area respectively in a predetermined range with luminance exceeding a predetermined threshold and have luminance respectively being more than a predetermined number of times as high as in a periphery section thereof.

Further, the second imaging device may be a digital camera which electrically stores image data of the side posture of the operator in memory, and the distance A from the operational manipulating position to the carrier lenses and the horizontal distance B from the operational manipulating position to the vertical line passing through the carrier lens in the direction perpendicular thereto measured in the step (e) may be calculated based on imaging magnification power of the second imaging device and a distance against the operator.

Further, the linear distances C, D from the right pupil position and the left pupil position of the operator to the operational manipulating position and the distance G from the center point of the frame to the operational manipulating position in the step (f) may be measured with a non-contact ranging device which is arranged at the operational manipulating position.

Further, the linear distances C, D from the right pupil position and the left pupil position of the operator to the operational manipulating position and the distance G from the center point of the frame to the operational manipulating position in the step (f) may be measured with laser measuring equipment or a ranging sensor using infrared light or ultrasonic waves.

Further, the determining of the downward wearing angles r1, r2 of the loupe units in the step (e) may be performed based on the distance A from the operational manipulating position to the carrier lenses, the distance B from the operational manipulating position to the vertical line passing through the carrier lens in the horizontal direction as being perpendicular thereto, and a downward forward-leaning angle s of the frame.

Further, the inward wearing angles p, q in the step (f) may be set to be smaller with increase of a corneal apex distance between a corneal of the operator and a back surface of the carrier lens.

Further, the forming of the opening portions for mounting the right and left loupe units in the step (g) may be performed by cutting with an NC processing machine.

Furthermore, the inserting and fixing of the right and left loupe units to the opening portions formed at the right and left carrier lenses in the step (g) may be performed in a state that the right and left loupe units and the right and left carrier lenses are positioned with laser positioning equipment at the downward wearing angles r1, r2 and the inward wearing angles p, q.

Further, according to the present invention, a method for manufacturing a binocular loupe in which loupe units are attached to carrier lenses mounted on a frame selected in accordance with an operator includes steps of (a) radiating strobe light from a below-located operational manipulating position in a state that the operator wearing the frame on which the carrier lenses are mounted stares the operational manipulating position in a working posture to use the binocular loupe, (b) photographing reflection light of the strobe light reflected from pupils of the operator with an imaging device which is arranged at the operational manipulating position, (c) electrically specifying a right pupil position (X1, Y1) and a left pupil position (X2, Y2) of the operator from a center point of the frame based on front image data obtained by the imaging device, (d) determining downward wearing angles r1, r2 of the loupe units which are to be attached to the carrier lenses based on output of an angular velocity sensor attached to the frame in the working posture, (e) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position, and (f) forming opening portions at the right and left carrier lenses based on the right pupil position, the left pupil position, the downward wearing angles r1, r2, and the inward wearing angles p, q, and inserting and fixing the right and left loupe units to the opening portions.

Furthermore, according to the present invention, a method for manufacturing a binocular loupe in which loupe units are attached to carrier lenses mounted on a frame selected in accordance with an operator includes steps of (a) radiating strobe light from a below-located operational manipulating position in a state that the operator wearing the frame on which the carrier lenses are mounted stares the operational manipulating position in a working posture to use the binocular loupe, (b) photographing reflection light of the strobe light reflected from pupils of the operator with a first imaging device which is arranged at the operational manipulating position, (c) obtaining side posture image data of the operator in the working posture with a second imaging device which is arranged at either or both of the right and left sides of the operator at a position or positions being apart therefrom by a predetermined distance, (d) electrically specifying a right pupil position (X1, Y1) and a left pupil position (X2, Y2) of the operator from a center point of the frame based on front image data obtained by the first imaging device, (e) measuring a distance A from the operational manipulating position to the carrier lenses in the working posture with a ranging sensor which is attached to the frame, measuring, from the side posture image data, a horizontal distance B from the operational manipulating position to a vertical line passing through the carrier lens in a direction perpendicular thereto, and determining downward wearing angles r1, r2 of the loupe units which are to be attached to the right and left carrier lenses based on the measured distance A and distance B, (f) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position, and (g) forming opening portions at the right and left carrier lenses based on the right pupil position, the left pupil position, the downward wearing angles r1, r2, and the inward wearing angles p, q, and inserting and fixing the right and left loupe units to the opening portions.

With the method for manufacturing a binocular loupe according to the present invention, an operator wearing a frame takes a working posture, strobe light is radiated toward the face section of the operator from an operational manipulating position at which the operator operates at hand, and reflected light is photographed with an imaging device so as to detect pupil positions from the photographed image. Accordingly, the pupil positions can be accurately specified in accordance with the working posture, so that a binocular loupe can be manufactured appropriately for each operator.

DETAILED DESCRIPTION OF THE PREFERRED EMBODIMENT

In the following, embodiments of a method for manufacturing a binocular loupe according to the present invention will be described in detail with reference to the attached drawings.

First Embodiment

First, the present method for manufacturing a binocular loupe also starts with selecting a frame which fits to a head section and a face section of an operator.

(Specifying Pupil Position)

Figure 4:
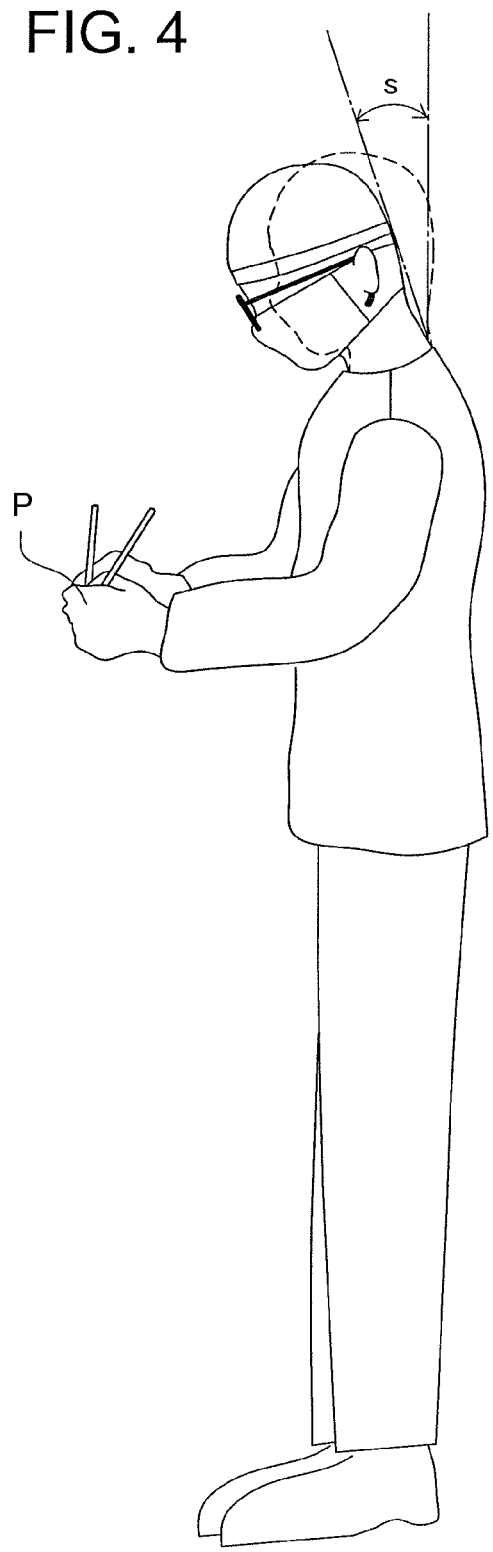
FIG. 4 is an explanatory view illustrating a state that an operator is working.
Figure 5:
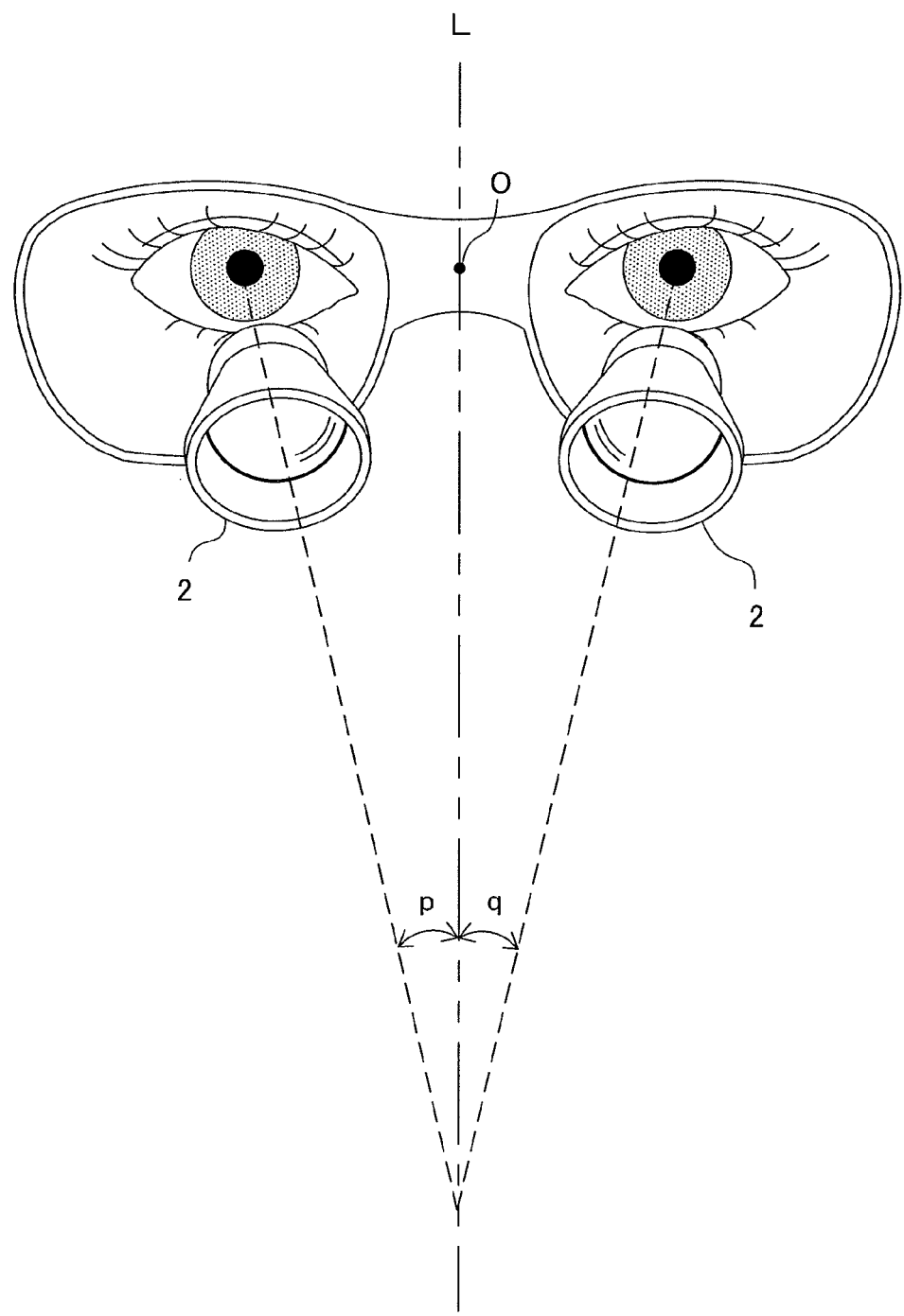
FIG. 5 is an explanatory view illustrating that loupe units are attached to carrier lenses as being inclined toward an operational manipulating position to be viewed.

With the method for manufacturing a binocular loupe according to the present invention, an operator takes a working posture (see FIG. 4) in a state of wearing a frame 1 on which loupe units 2 are not mounted. Then, strobe light is radiated toward the face section of the operator from an operational manipulating position P at which the operator actually operates at hand and photographing is performed with a camera 11A (a first imaging device), so that pupil positions are specified.

Figure 8:
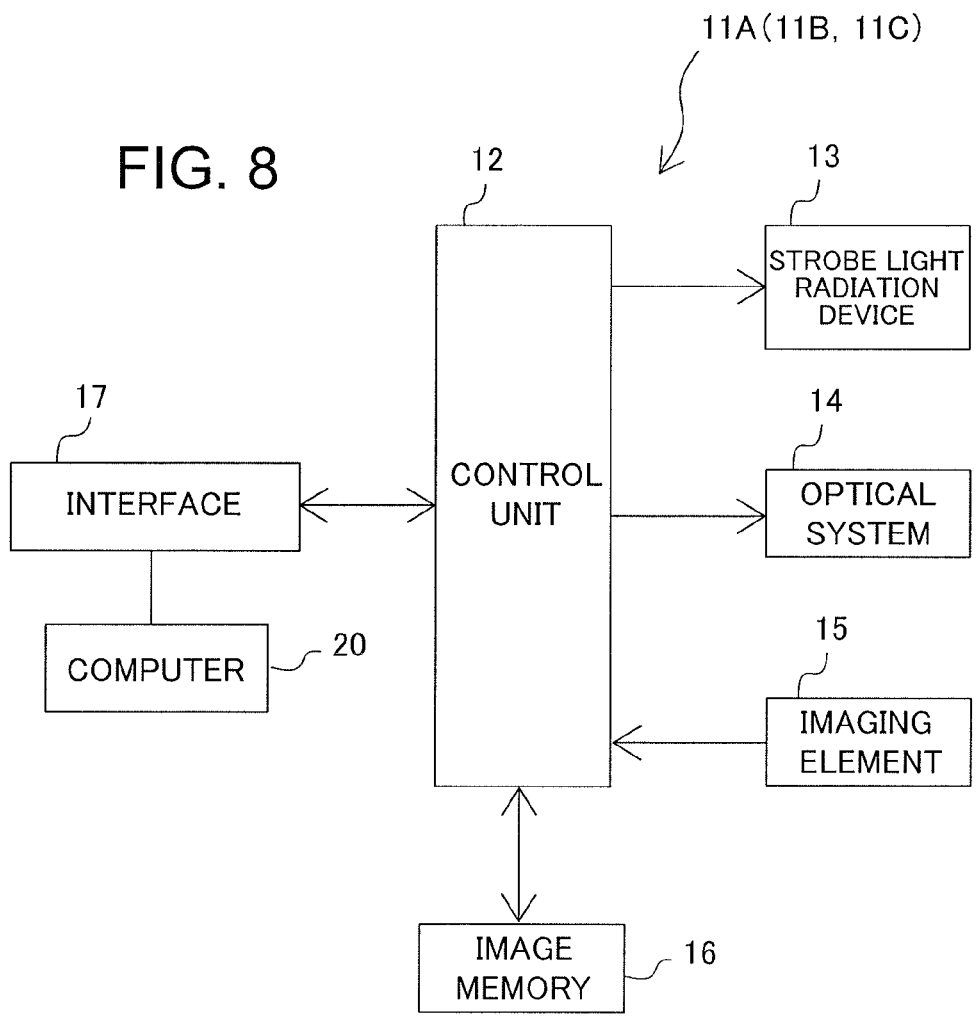
FIG. 8 is a block diagram schematically illustrating a configuration of the camera.

Next, specifying of pupil positions using the camera 11A will be specifically described. FIG. 8 schematically illustrates a configuration of the camera 11A. The camera 11A is a digital camera including a control unit 12, a strobe light radiation device 13, an optical system 14, an imaging element 15, an image memory 16, and an interface 17 for performing transmitting and receiving of data and signals with a computer 20 which performs an imaging process.

The control unit 12 includes a memory portion of a program which controls each part of the camera 11A, and a CPU which executes the program. The control unit 12 performs control such as control of the optical system 14 for imaging magnification power, focusing and the like in accordance with instructions from the computer 20 and a control of storing, reading, and the like of an image against the image memory 16.

Figure 9:
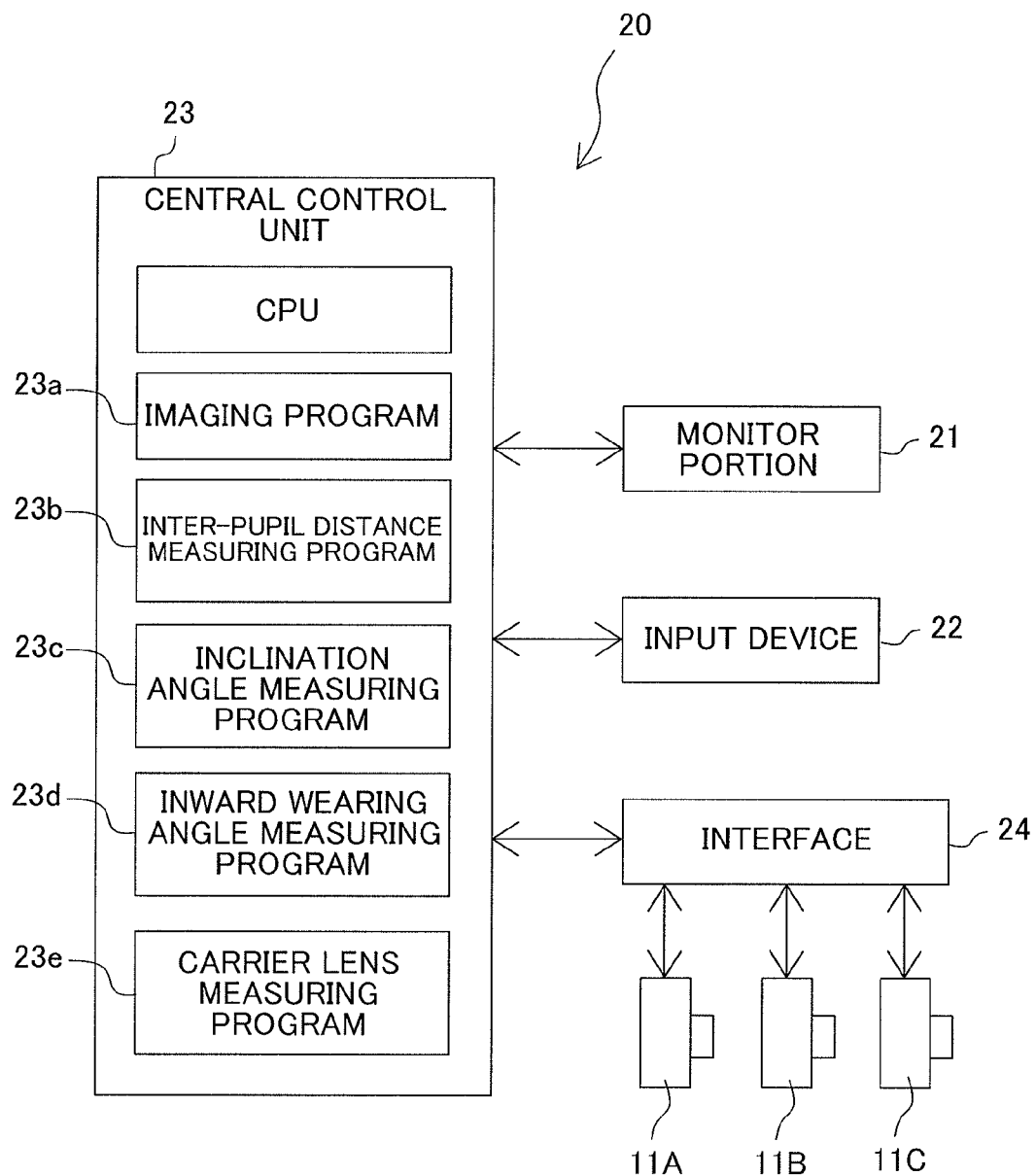
FIG. 9 is a block diagram schematically illustrating a configuration of a computer.

FIG. 9 schematically illustrates a configuration of the computer 20. The computer 20 includes a monitor portion 21, an input device 22, a central control unit 23 which performs specific arithmetic processing and control processing based on the program, and an interface 24 which performs transmitting and receiving of data and signals with the camera 11A (first imaging device). Further, a camera 11B and a camera 11C (both are second imaging devices) are connected to the interface 24. These cameras will be described later.

The central control unit 23 includes an imaging program 23a, an inter-pupil distance measuring program 23b, an inclination angle measuring program 23c, an inward wearing angle measuring program 23d, a carrier lens measuring program 23e, and a central processing unit CPU which executes the programs.

The computer 20 causes the camera 11A to operate for measuring an inter-pupil distance. Here, the central control unit 23 controls the camera 11A by executing the imaging program 23a, so that a focal distance is matched to the center point O of the frame 1 (FIG. 7) with zooming to both eyes of the operator wearing the frame 1. In accordance with instructions from the computer 20, the camera 11A outputs to the computer 20 an image signal which is taken by the optical system 14 and converted into an electric signal by the imaging element 15. Then, the computer 20 causes the monitor portion 21 to display the image. Accordingly, a manufacturer of a binocular loupe can provide instructions through the input device 22 for adjustment such as a range and positioning of the image photographed by the camera 11A. The computer 20 adjusts the image photographed by the camera 11A in accordance with the adjustment instructions.

In response to a photographing instruction transmitted from the computer 20 under instructions of the manufacturer of a binocular loupe, the camera 11A performs photographing while radiating strobe light from the strobe light radiation device 13. The imaging element 15 of the camera 11A converts light for photographing from the optical system 14 into an electric signal and outputs the signal to the control unit 12. The control unit 12 stores the image data in the image memory 16.

The central control unit 23 of the computer 20 executes the inter-pupil distance measuring program 23b, so that the image data stored in the image memory 16 of the camera 11A is read and displayed on the monitor portion 21. When photographing is performed with strobe light, the light is reflected from pupils of both eyes. Accordingly, luminance thereat becomes high among the image data.

Figure 7:
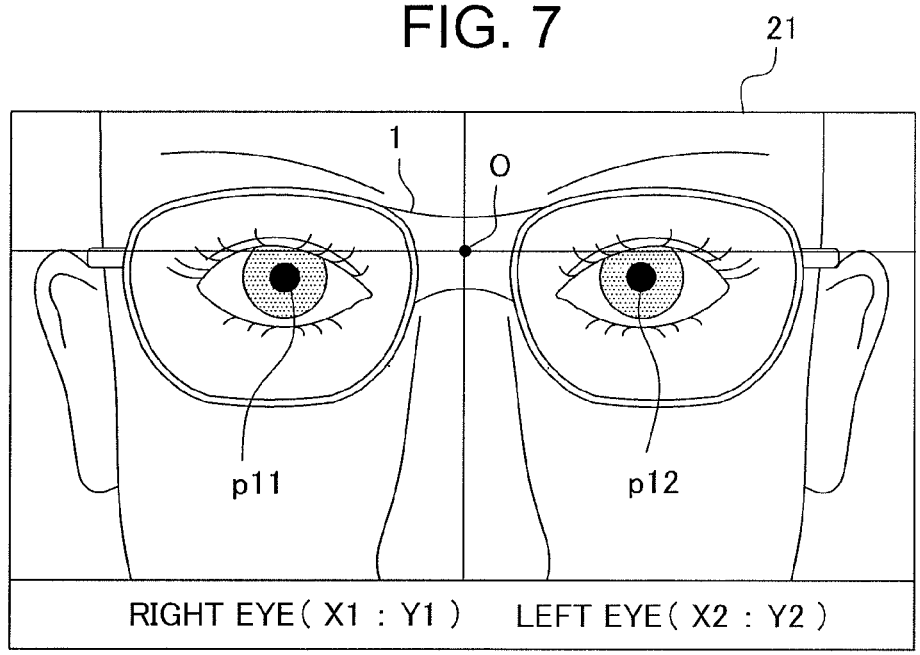
FIG. 7 is an explanatory view of a screen on a monitor when the operator wearing the frame is photographed by a camera for measuring the inter-pupil distance.

FIG. 7 illustrates a screen displayed on the monitor portion 21 at that time. The central control unit 23 performs scanning of pixels in predetermined sections of the image data at right and left sides from the center point O of the frame 1 and detects a section in which luminance exceeds a predetermined threshold. Then, arithmetic processing is performed to determine center points p11, p12 of segments which have area respectively in a predetermined range with luminance exceeding the threshold and which have luminance respectively being more than a predetermined number of times as high as in a periphery section thereof, so that a right pupil position (X1, Y1) and a left pupil position (X2, Y2) of the operator are electrically specified.

Other than specifying right and left pupil positions of the operator owing to that the central control unit 23 performs scanning with calculation of imaging element luminance, the manufacturer may point out the right pupil position p11 and the left pupil position p12 in the image displayed on the monitor portion 21 directly with the input device 22 such as a mouse. In this case, the central control unit 23 calculates the pointed-out positions and electronically specifies the right pupil position (X1, Y1) and the left pupil position (X2, Y2).

(Determining Downward Wearing Angle of Loupe Unit)

A downward wearing angle of the loupe unit 2 is determined by the central control unit 23 executing the inclination angle measuring program 23c. In this case, the central control unit 23 controls the camera 11B and the camera 11C (both are second imaging devices) to photograph a working posture of the operator simultaneously from the right side and the left side. As being the same as the camera 11A, description of the configuration of the cameras 11B, 11C will not be repeated.

Figure 6:
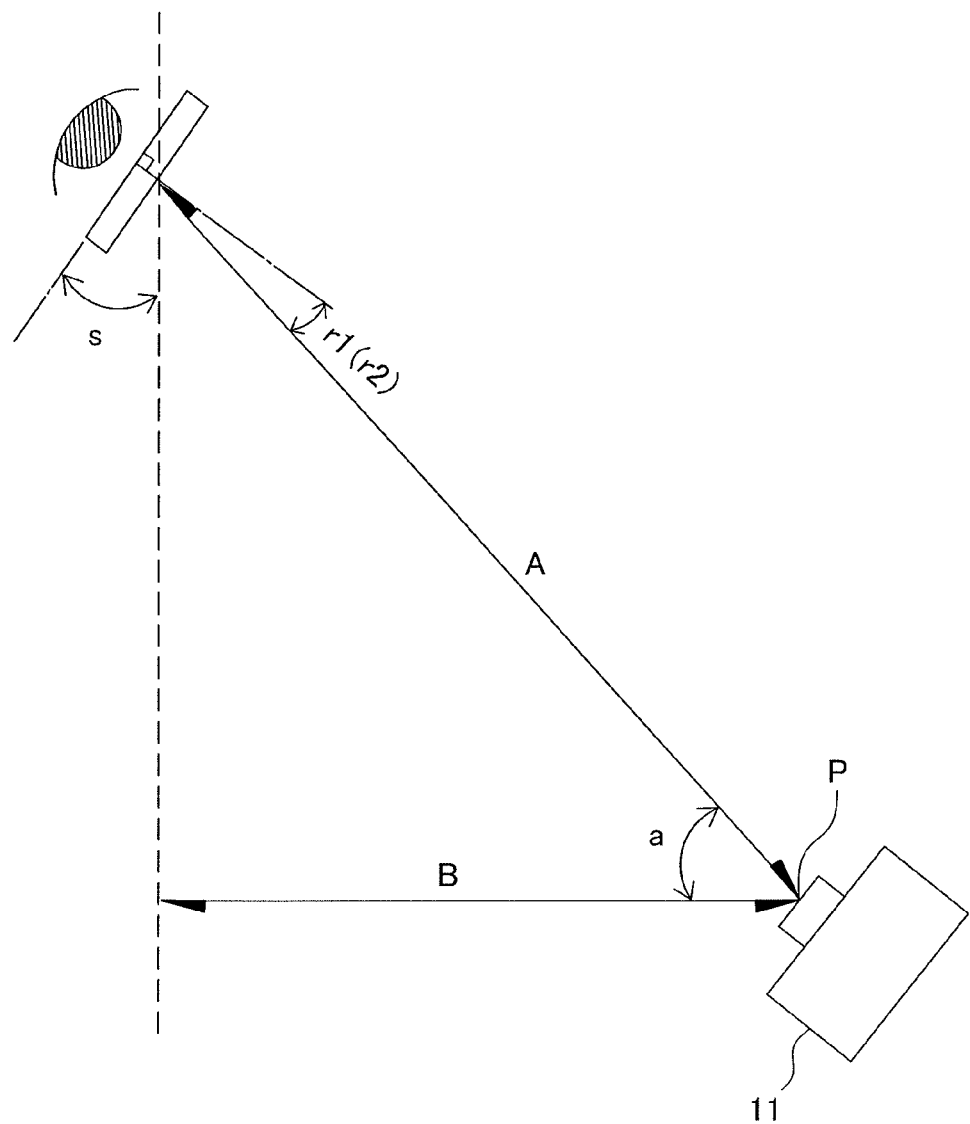
FIG. 6 is an explanatory view schematically illustrating a state that an operator wearing a frame takes a working posture.
Figure 10:
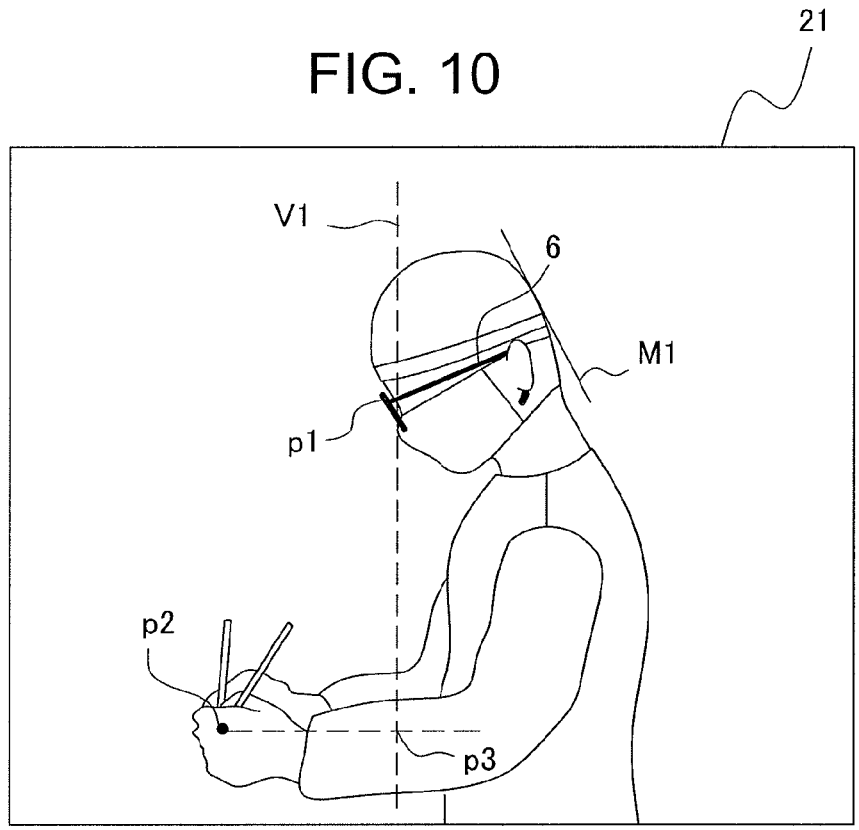
FIG. 10 is an explanatory view of a screen on a monitor displaying an image in a state that the operator is working photographed from the left side.

The central control unit 23 reads out image data photographed from the left side and stored in the image memory 16 of the camera 11B and causes the monitor portion 21 to display an image as illustrated in FIG. 10. The manufacturer of a binocular loupe points out, directly with the input device 22 such as a mouse, two points being a point p1 at a left connecting part of a frame temple portion 6 and the frame 1 and a point p2 at the operational manipulating position on the display screen. Then, the central control unit 23 calculates an actual distance therebetween from a distance between the point p1 and the point p2 on the screen and imaging magnification power of the camera 11B and displays the result. The calculated distance corresponds to a distance A (FIG. 6) between the operational manipulating position P and a left carrier lens 5.

Similarly, the manufacturer points out, on the display screen, two points being the point p2 at the operational manipulating position and a point p3 at which a horizontal line therefrom and a vertical line V1 passing through the left carrier lens 5 bisect at right angles. Then, the central control unit 23 calculates an actual distance therebetween from a distance between the point p2 and the point p3 on the screen and the imaging magnification power and displays the result. The calculated distance corresponds to a horizontal distance B (FIG. 6) from the operational manipulating position P to a point at which a horizontal line therefrom and the vertical line V1 passing through the left carrier lens 5 bisect at right angles.

Further, the manufacturer draws, on the screen, an inclination line M1 at the back of the head of the operator against the vertical line V1 passing through the backbone of the operator. Then, the central control unit 23 calculates a forward-leaning angle s of the frame 1 illustrated in FIG. 4 and displays the result.

Figure 11:
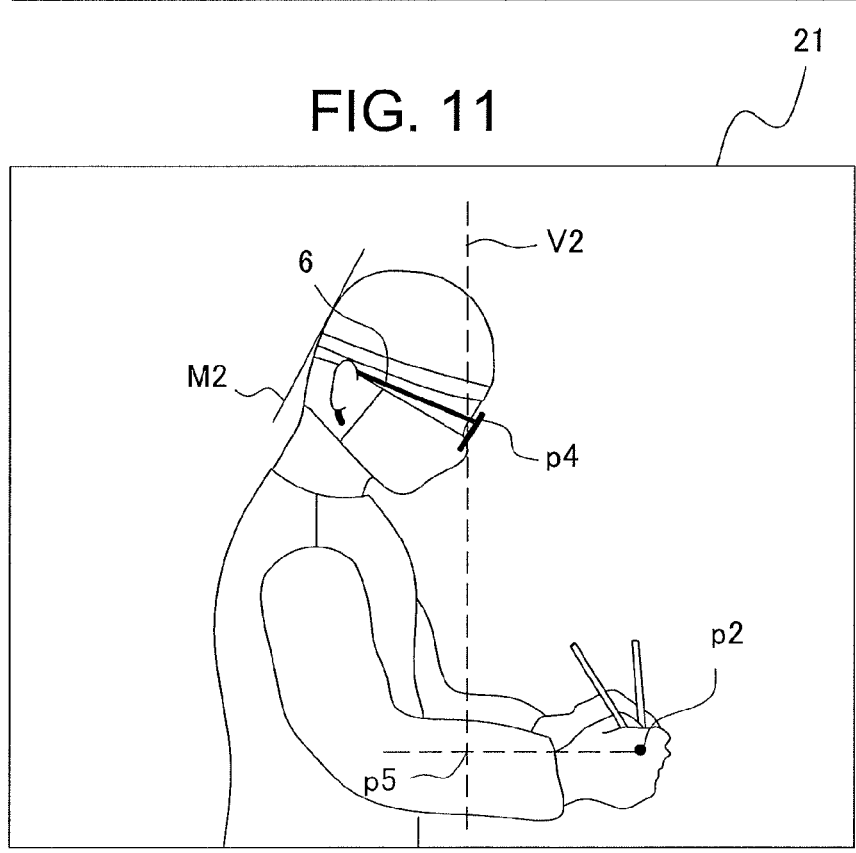
FIG. 11 is an explanatory view of a screen on a monitor displaying an image in a state that the operator is working photographed from the right side.

Further, the central control unit 23 reads out image data stored in the image memory 16 of the camera 11C and causes the monitor portion 21 to display an image as illustrated in FIG. 11. The manufacturer of a binocular loupe points out, directly with the input device 22 such as a mouse, two points being a point p4 at a right connecting part of a frame temple portion 6 and the frame 1 and a point p5 at the operational manipulating position on the display screen. Then, the central control unit 23 calculates an actual distance therebetween from a distance between the point p4 and the point p5 on the screen and imaging magnification power of the camera 11C and displays the result. The calculated distance corresponds to a distance A (FIG. 6) between the operational manipulating position P and a right carrier lens 5.

Similarly, the manufacturer points out two points being the point p2 at the operational manipulating position and a point p5 at which a horizontal line therefrom and a vertical line V2 passing through the right carrier lens 5 bisect at right angles. Then, the central control unit 23 calculates an actual distance therebetween from a distance between the point p2 and the point p3 on the screen and the imaging magnification power and displays the result. The calculated distance corresponds to a horizontal distance B (FIG. 6) from the operational manipulating position P to a point at which a horizontal line therefrom and the vertical line V2 passing through the right carrier lens 5 bisect at right angles.

Further, the manufacturer draws, on the screen, an inclination line M2 at the back of the head of the operator against the vertical line V2 passing through the backbone of the operator. Then, the central control unit 23 calculates a forward-leaning angle s of the frame 1 illustrated and displays the result.

A left half and a right half of a human body are not entirely symmetric against the center line thereof. Therefore, it is preferable that the working posture is photographed from both right and left sides and the distance A from the operational manipulating position P to the carrier lens 5 and the horizontal distance B from the operational manipulating position P to the vertical line passing through the carrier lens 5 in the horizontal direction as being perpendicular thereto are measured from the respective images with the both eyes, respectively. Further, there may be a case that some operator takes a posture in which a dominant eye is closer to a target for better observation at the operational manipulation position P. In such a case, the forward-leaning angle s of the frame 1 differs between the right and left. Accordingly, it is preferable that the forward-leaning angle s of the frame 1 is obtained from the right and left photographed images, respectively.

Then, the central control unit 23 determines downward wearing angles r1, r2 (FIG. 6) of the loupe units 2 which are mounted on faces of the right and left carrier lenses 5 based on the distance A from the operational manipulating position P to the carrier lenses 5 and the horizontal distance B from the operational manipulating position P in a direction perpendicular to the vertical line passing through the carrier lens 5, which are obtained from the photographed images of both the right and left sides of the working posture, and the forward-leaning angle s of the frame 1 which is worn by the operator.

Here, it is also possible to obtain the downward wearing angles r1, r2 being common to both right and left based on the distance A from the operational manipulating position P to the carrier lens 5 and the horizontal distance B from the operational manipulating position P to the vertical line passing through the carrier lens 5 in a direction perpendicular thereto, which are obtained from the image photographed from either the right side or the left side, and the forward-leaning angle s of the frame 1. Note that the above does not depart from the scope of the present invention.

Further, the forward-leaning angle s of the frame 1 which is worn by the operator may not be obtained from the screen as described above. It is also possible to set, in the inclination angle measuring program 23c, the forward-leaning angle s of the frame 1 based on a statistical result that the forward-leaning angle of the head of an operator is to be 25 degrees in a standing posture or 20 degrees in a sitting posture. However, in such a case, there may be a case that forward-leaning angles differ remarkably among operators.

Further, when photographing with the camera 11A from the front of the operator and photographing with the camera 11B and the camera 11C from both right and left sides of the operator, data can be obtained in the same working posture. Consequently, data can be obtained with integrity. However, it is also possible to perform the above photographing separately. When the above photographing is performed separately, one or two cameras maybe commonly used. In this case, the measurement data lack integrity owing to difference among working postures of the operator for photographing.

As another example to measure the distance A from the operational manipulating position P to the carrier lens 5, it is also possible to adopt a method to perform actual measurement using a compact ranging sensor. A ranging sensor radiates infrared light to an object, measures an amount of infrared light reflected from the object, and outputs voltage corresponding to the strength of the reflected light. When the ranging sensor is attached to a bridge (a center part contacting to the glabella when worn) of the frame 1 and an operator wearing the frame 1 takes a working posture, the ranging sensor outputs voltage corresponding to the distance A from the center of the frame 1 to the operational manipulating position P. Accordingly, it is possible to obtain a value of the distance A owing to that arithmetic processing is performed on a signal value of the voltage by the computer 20. Alternatively, it is also possible to use a ranging sensor which performs ranging using laser light or ultrasonic waves other than infrared light. In this case, measurement is based on time from emitting laser light or ultrasonic waves until returning thereof after being reflected by an object.

(Measuring Distance from Right Eye and Left Eye to Operational Manipulating Position)

Figure 12:
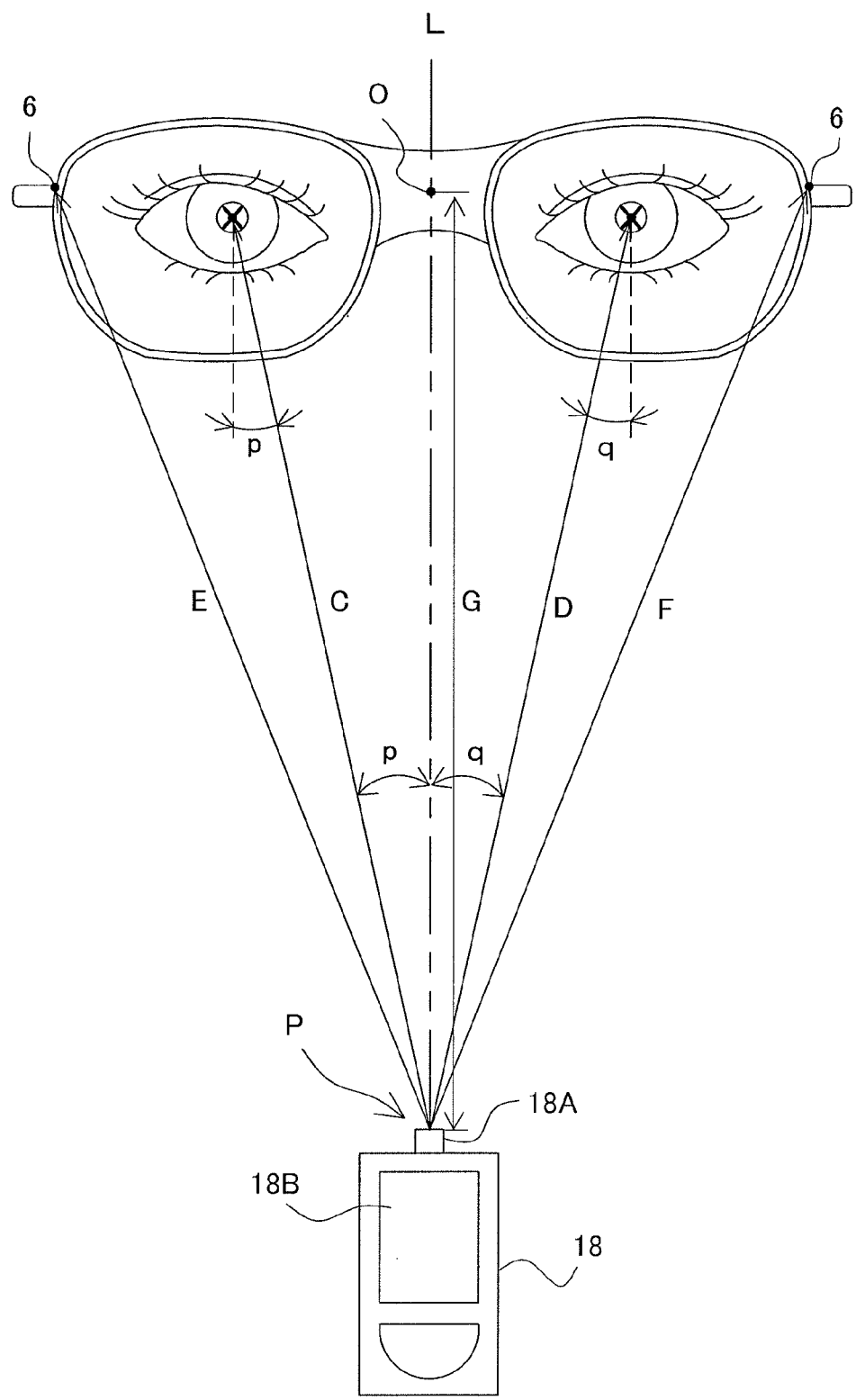
FIG. 12 is an explanatory view schematically illustrating measurement of distances from the operational manipulating position to positions of the right and left carrier lenses corresponding to pupils using laser measuring equipment.

Inward wearing angles p, q for mounting the right and left loupe units 2 on the carrier lenses 5 are determined by the central control unit 23 executing the inward wearing angle measuring program 23d. As illustrated in FIG. 12, the inward wearing angles p,q of the loupe units 2 to be mounted on the right and left carrier lenses 5 are determined based on linear distances C, D from the right pupil position and the left pupil position of the operator to the operational manipulating position P and a distance G from the center point O of the frame 1 to the operational manipulating position P.

The central control unit 23 previously specifies the right pupil position (X1, Y1) and the left pupil position (X2, Y2). Further, since the center point O is focused, the distance G from the operational manipulating position P to the center point O of the frame 1 is obtained from the focal distance of the photographing. Accordingly, the central control unit 23 calculates the distance G and the linear distances C, D from the right pupil position (X1, Y1) and the left pupil position (X2, Y2) of the operator to the operational manipulating position P, and then, calculates the inward wearing angles p, q, respectively.

Figure 2:
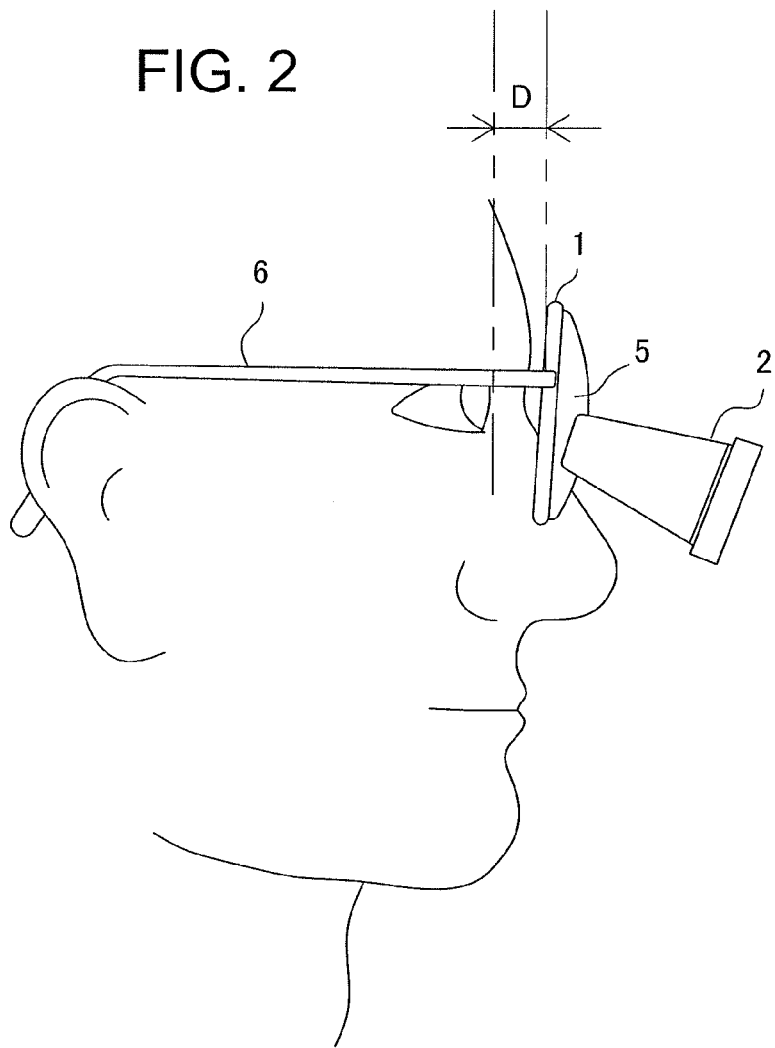
FIG. 2 is a structural view illustrating a state that the binocular loupe is worn.
Figure 3:
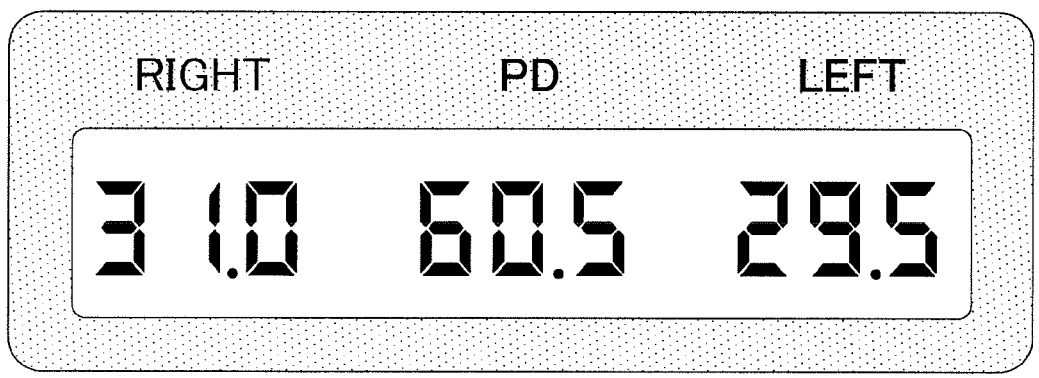
FIG. 3 is an explanatory view illustrating a state that an inter-pupil distance measured by a PD meter is displayed.
Figure 17:
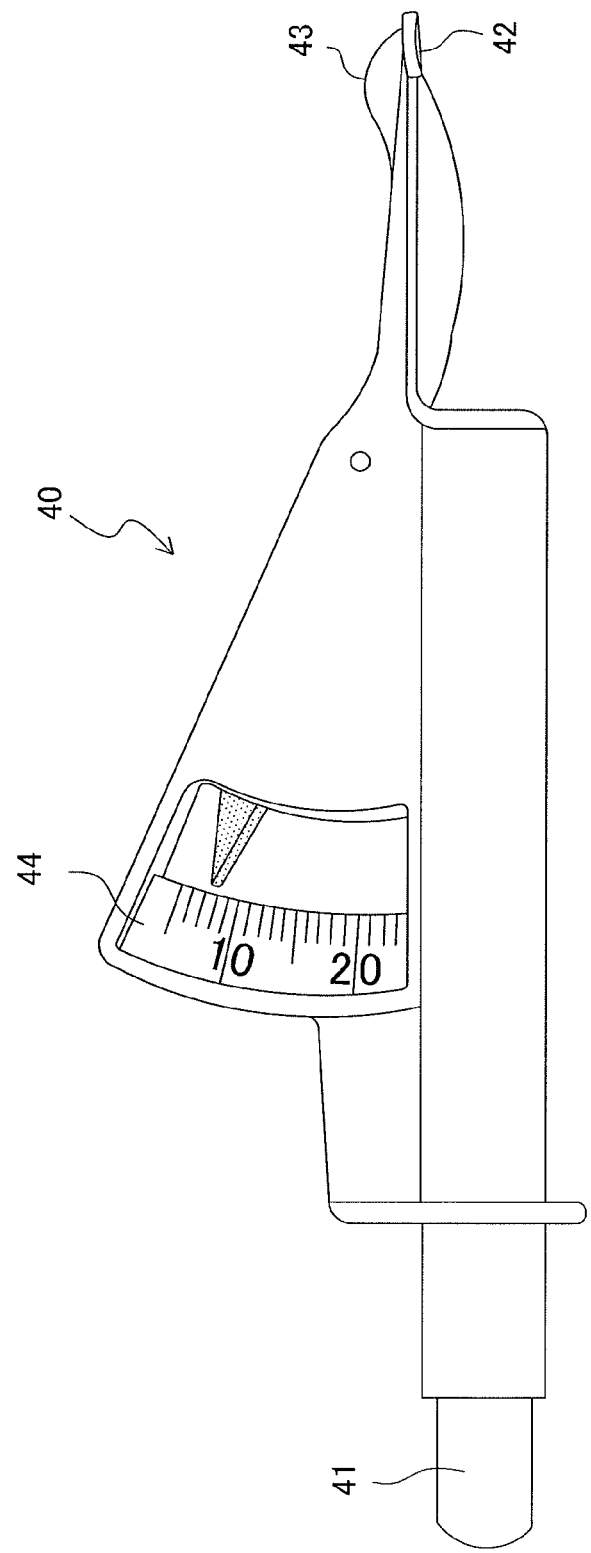
FIG. 17 is an explanatory view illustrating a schematic configuration of corneal apex distance measuring equipment.

When a corneal apex distance D (FIG. 2) is took into account for the inward wearing angles p, q, it is possible to manufacture a more practical binocular loupe. As illustrated in FIG. 2, the corneal apex distance denotes a distance between a corneal of the operator wearing the frame 1 and a back surface of the carrier lens 5. For measuring the corneal apex distance, a distance between a surface of an eyelid and an inner surface of a lens is actually measured for each of both eyes in a state that the eyes of the operators are closed. There exists measuring equipment dedicated for the measurement. FIG. 17 illustrates a configuration of corneal apex distance measuring equipment 40. A top end part thereof is inserted between the corneal of the operator and the back surface of the carrier lens 5, a corneal contacting portion 42 and a lens contacting portion 43 are moved mutually in opposite directions to be opened like scissors by depressing an operation portion 41, so that the corneal contacting portion 42 is contacted to the corneal and the lens contacting portion 43 is contacted to the back surface of the carrier lens 5. The corneal apex distance is denoted by a value of a scale portion 44 indicating the opened distance therebetween in the above state.

When the operator wears the frame 1, a range of view of the operator becomes narrow in accordance with the corneal apex distance D. Therefore, it is preferable that the inward wearing angles p,q for attaching the right and left loupe units 2 to the carrier lenses 5 are corrected to be small in accordance with the value of the corneal apex distance D.

Thus, the inward wearing angle measuring program 23d which is to be executed by the central control unit 23 is programmed to appropriately correct the inward wearing angles p, q in accordance with a value of the corneal apex distance D when the value is input with the input device 22. According to the above, the central control unit 23 provides the inward wearing angles p, q which are practically appropriate to ensure a view angle when the loupe units 2 for both eyes are attached to the carrier lenses 5 as being inwardly oriented toward the operational manipulating position P respectively.

Here, the linear distances C, D from the right pupil position (X1, Y1) and the left pupil position (X2, Y2) of the operator to the operational manipulating position P and the distance G from the operational manipulating position P to the center point O of the frame 1 may be measured and the measurement values may be input with the input device 22. In this case, the central control unit 23 calculates the inward wearing angles p, q based on the measurement values input with the input device 22. Subsequently, when the corneal apex distance D is input, the central control unit 23 calculates and provides the corrected inward wearing angles p, q.

The actual measurement thereof is performed by measuring distances from the operational manipulating position P to marks (marks X) indicated on the right and left carrier lenses 5 corresponding to the right pupil position (X1, Y1) and the left pupil position (X2, Y2) of the operator electrically specified by measuring the inter-pupil distance with the computer 20. The actual measurement may be performed with a scale. Alternatively, it is possible to use laser measuring equipment 18, illustrated in FIG. 12, which is widely used at sites of construction measurement. Following is measurement procedure of the above. First, laser shielding is performed on the face of the operator and the laser measurement equipment 18 is set at the operational manipulating position P on the center line L passing through the center point O of the frame 1. Then, in the above state, each of the respective distances C, D to the mark position on the right or left carrier lens 5 is measured while the laser measuring equipment 18 is laterally swung so that laser light from a laser radiating port 18A hits the marking position without changing location of the laser measuring equipment 18. According to the above, measurement values of the inward wearing angles p, q from the center line L are displayed on a display portion 18B of the laser measuring equipment 18 along with the respective distances C, D. Other than such laser measuring equipment 18, a ranging sensor using infrared light or ultrasonic waves as described above may be used for measuring the distances C, D.

(Measuring Downward Wearing Angle with Laser Measuring Equipment)

It is also possible to use such laser measuring equipment 18 for measuring the downward wearing angles r1, r2 of the abovementioned loupe units 2. Following description is performed as replacing the camera 11 with the laser measuring equipment 18 in FIG. 6. The laser measuring equipment 18 is placed on the center line L in FIG. 12, and then, laser light is radiated while the laser radiating port 18A is oriented toward the connecting part of the frame temple portion 6 and the frame 1. Thus, the distance A and the angle a are measured by the laser measuring equipment 18 and displayed on the display portion 18B.

Then, the downward wearing angles r1, r2 when attaching the right and left loupe units 2 to the carrier lenses 5 are determined by a measurer based on the angle a which is measured with the laser measuring equipment 18 and the forward-leaning angle of the frame 1 worn by the operator as being approximately equal to 25 degrees or 20 degrees.

(Attaching Loupe Unit to Carrier Lens)

Programming for positions of the carrier lenses 5 to which the loupe units 2 are inserted is performed on an NC processing machine based on the downward wearing angles r1, r2 and the inward wearing angles p, q obtained as described above as well as the values of the right pupil position (X1, Y1) and the left pupil position (X2, Y2) obtained from the image data. Then, opening portions are formed at the carrier lenses 5 by performing cutting at insertion portions.

After the opening portions are formed, the loupe units 2 are inserted to the carrier lenses 5 through the opening portions.

The downward wearing angles r1, r2 and the inward wearing angles p, q are adjusted by laser positioning equipment, and then, the loupe units 2 are fixed to the carrier lenses 5 with attaching portions 3. The attaching portion 3 includes an adapter which fixes the loupe unit 2, and a ring which tightens the adapter in a state that the carrier lens 5 is sandwiched. The adapter is configured to fix the loupe unit 2 as holding at the downward wearing angle r1, r2 and the inward wearing angle p, q against the surface of the carrier lens 5. Alternatively, the loupe unit 2 may be fixed to the carrier lens 5 with adhesion bond after the loupe unit 2 is inserted to the opening portion in a state of being held at the downward wearing angle r1, r2 and the inward wearing angle p, q.

(Manufacturing Carrier Lens)

The carrier lens 5 is for correcting eyesight such as near-sightedness and far-sightedness of an operator. The carrier lens 5 maybe a bifocal lens for near-sight and far-sight. When an operator does not require eyesight correction, a lens without prescription is used.

The carrier lenses 5 are manufactured before the loupe units 2 are attached, that is, at the time when the frame 1 is selected by the operator. At that time, when the operator requires eyesight correction, focal distances of the lenses can be measured by radiating strobe light to the face section of the operator.

In this case, strobe light is radiated to the face section of the operator and photographing is performed while the central control unit 23 executes the imaging program 23a and controls the camera 11A as being the same as the case of specifying the pupil positions. Here, the operator looks into distance above the operational manipulating position P in a natural standing posture not in a working posture. Then, a focal distance is matched to the center point O of the frame 1 with zooming to both eyes of the operator wearing the frame 1. Based on instructions from the computer 20, the camera 11A placed at the operational manipulating position P outputs, to the computer 20, an image signal which is taken by the optical system 14 and converted into an electrical signal by the imaging element 15. The computer 20 displays the image on the screen of the monitor portion 21, so that the manufacturer of an binocular loupe can provide instructions with the input device 22 for adjustment of a range, positioning, and the like of the photographed image. The computer 20 controls the camera 11A in accordance with the instructions for adjustment.

In response to a photographing instruction transmitted from the computer 20, the camera 11A performs photographing while radiating strobe light from the strobe light radiation device 13. The imaging element 15 of the camera 11A converts light for photographing from the optical system 14 into an electric signal and outputs the signal to the control unit 12. The control unit 12 stores the image data in the image memory 16.

Figure 13:
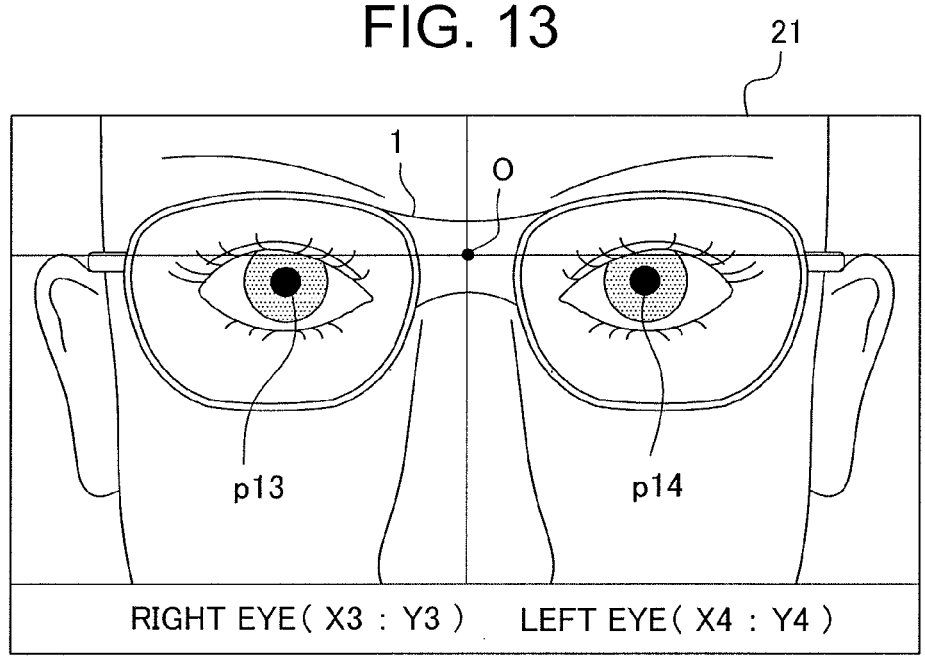
FIG. 13 is an explanatory view of a screen on a monitor when the operator wearing the frame is photographed by the camera for measuring a focal distance of carrier lenses for correcting eyesight.

Owing to control of the carrier lens measuring program 23e, the central control unit 23 of the computer 20 reads out the image data stored in the image memory 16 of the camera 11A and causes the monitor portion 21 to display the image. As described above, when photographing is performed with strobe light, luminance at the pupil positions of both eyes becomes high compared to that at the periphery. The monitor portion 21 displays the image as illustrated in FIG. 13.

The central control unit 23 performs scanning of pixels in predetermined sections of the image data at right and left sides from the center point O of the frame 1 and detects a section in which luminance exceeds a predetermined threshold. Then, arithmetic processing is performed to determine center points p13, p14 of segments which have area respectively in a predetermined range with luminance exceeding the threshold and which have luminance respectively being more than a predetermined number of times as high as in a periphery section thereof, so that a right pupil position (X3, Y3) and a left pupil position (X4, Y4) of the operator are electrically specified.

Further, as an alternative method as described above, the manufacturer may point out the right pupil position p13 and the left pupil position p14 in the image displayed on the monitor portion 21 directly with the input device 22 such as a mouse, so that the central control unit 23 electrically specifies the right pupil position (X3, Y3) and the left pupil position (X4, Y4).

Then, the right and left carrier lenses 5 are processed so that the centers of the lenses for eyesight correction are matched to the right pupil position (X3, Y3) and the left pupil position (X4, Y4) of the operator. When using such a binocular loupe having the carrier lenses 5 capable of correcting eyesight of the operator, the operator can stare a precise section through the loupe units 2 in an enlarged manner during working and can ensure a range of corrected view through the carrier lenses 5 in a natural posture after releasing the working posture. The above saves the operator the bother of replacing a binocular loupe with glasses each time for working preparation, working adjustment with other persons, and the like.

(Configuration of Focal Point Adjusting Portion of Loupe)

Figure 1:
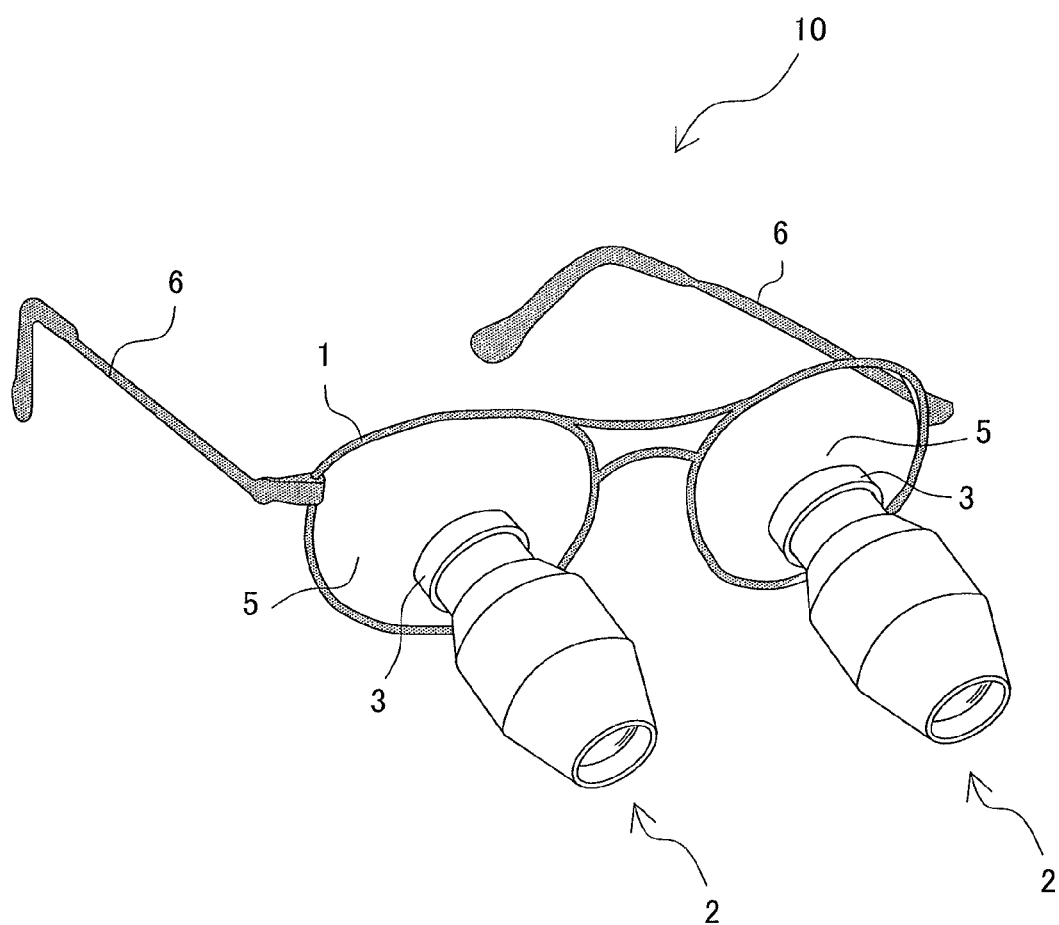
FIG. 1 is a structural view illustrating an entire configuration of a binocular loupe.
Figure 14:
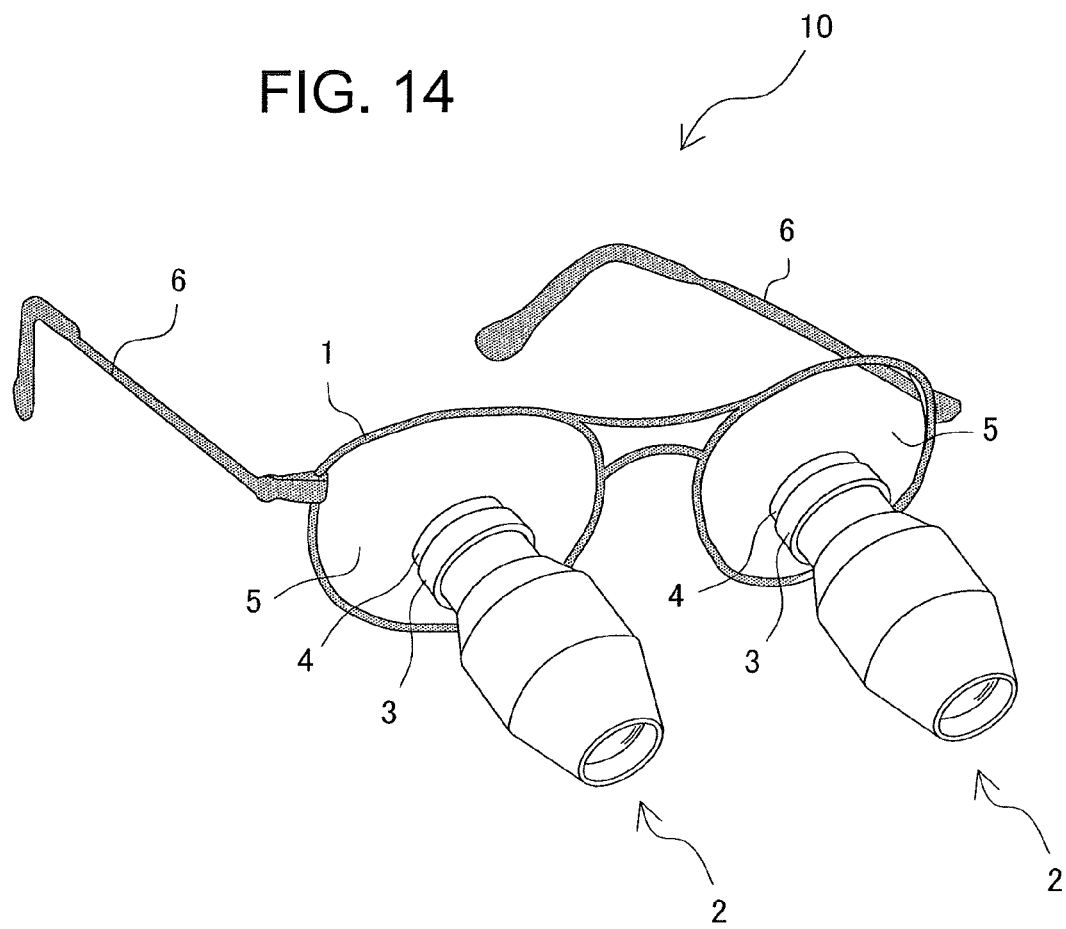
FIG. 14 is a structural view illustrating an entire configuration of a binocular loupe on which loupe units with focal point adjusting portions attached are mounted.

Here, it is possible to add a function of adjusting a focal point to the loupe units 2 in accordance with eyesight of the operator. FIG. 14 illustrates the binocular loupe 10 on which the loupe units 2 with focal point adjusting portions 4 attached are mounted. The configuration and description thereof with the exception of the focal point adjusting portions 4 are the same as those of the binocular loupe 10 illustrated in FIG. 1. A focal point adjusting lens unit which is detachably attachable is assembled into the focal point adjusting portion 4 for finely adjusting a focal point in accordance with an operational distance of the loupe unit 2. Here, it is possible to select among a plurality of lens units having different specifications in accordance with current eyesight of the operator.

Figure 15:
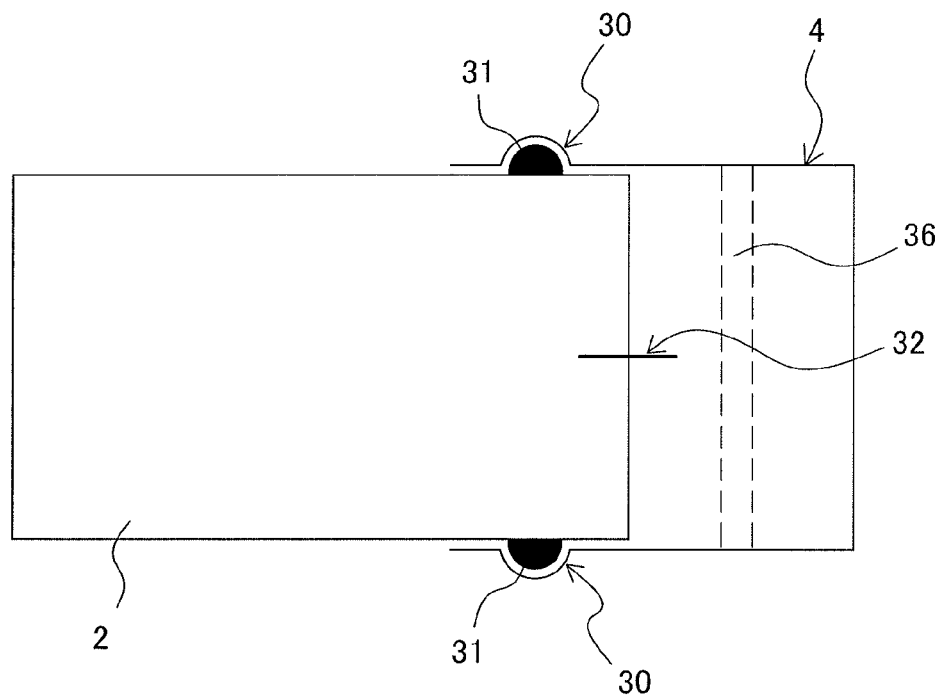
FIG. 15 is a plane view illustrating an example of a configuration to attach a focal point adjusting portion to a loupe unit.
Figure 16:
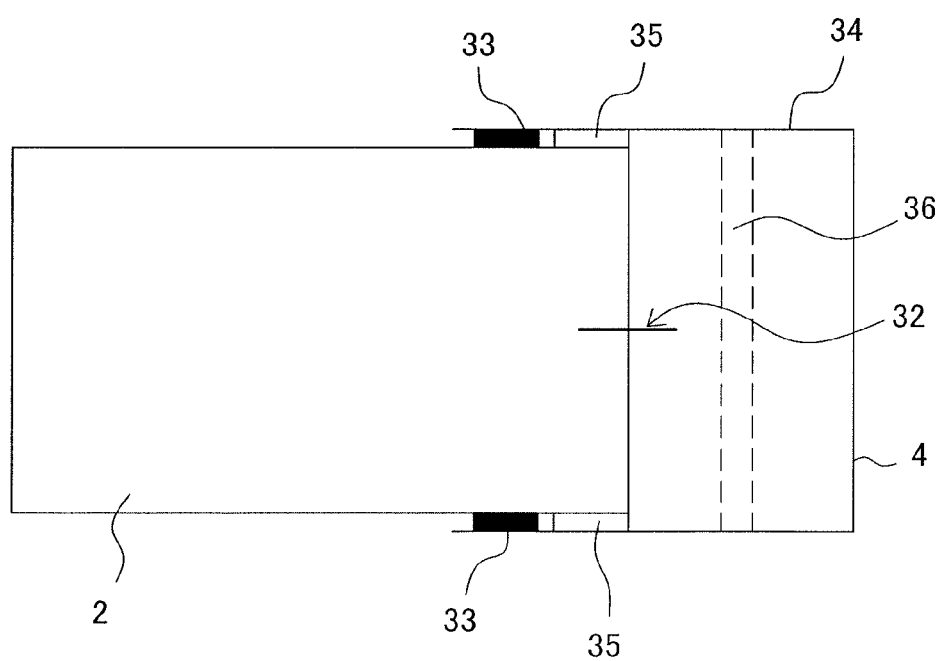
FIG. 16 is a plane view illustrating another example of a configuration to attach a focal point adjusting portion to a loupe unit.

FIGS. 15 and 16 illustrate examples to attach the focal point adjusting portion 4 to the loupe unit 2. FIG. 15 illustrates an example of a fitting type and FIG. 16 illustrates an example of a magnetic type attaching with magnetic force in a detachably attachable manner. In the case of the fitting type illustrated in FIG. 15, a concave portion 30 is arranged at the focal point adjusting portion 4 and a convex portion 31 is arranged at a rear part of the loupe unit 2. It is configured that the focal point adjusting portion 4 can be attached to an ocular part of the loupe unit 2 by fitting the convex portion 31 to the concave portion 30.

Accurate positioning of the focal point adjusting portion 4 can be performed by aligning positioning lines 32 at the time of attaching thereof. Owing to that the positioning lines 32 are arranged for positioning, the focal point adjusting portion 4 performs attaching at the right position even when the lens unit has magnification power directivity corresponding to a case of astigmatism or the like. Further, the focal point adjusting portion 4 can be removed from the loupe unit 2 in the order opposite to the above.

Here, an inner diameter of the focal point adjusting portion 4 is set to be slightly larger than an outer diameter of the loupe unit 2 at the rear part. Further, the focal point adjusting portion 4 is formed flexible at a housing section in the vicinity of the concave portion 30. Accordingly, when the concave portion 30 arrives at the position of the convex portion 31 while the housing section of the focal point adjusting portion 4 in the vicinity of the concave portion travels toward the loupe unit 2 as depressing the convex portion 31, the convex portion 31 is firmly fitted to the concave portion 30.

In the case of the magnetic type illustrated in FIG. 16, a ferromagnetic metal plate 33 is arranged at the loupe unit side and a metal magnet (or a plastic magnet containing magnetized metal powder) 34 is arranged at the focal point adjusting portion 4 side. Both of the above are mutually attracted with magnetic force as being positioned by a stopper 35, so that the focal point adjusting portion 4 is attached to the loupe unit 2 in a detachably attachable manner. The configuration and description thereof with the exception of the above are the same as those of the fitting type illustrated in FIG. 15. Other than the above, the focal adjusting portion 2 may be attached to the loupe unit 2 in various manners. Further, although the focal point adjusting portion 4 is attached to the rear end (ocular part) of the loupe unit 2 in the above, it is also possible to attach the focal point adjusting portion 4 to the leading end side.

Further, the loupe unit 2 is provided with a lens unit 36 for magnification power adjustment being an optical system for enlarging an image of a working target with a lens series. For example, the lens unit 36 has magnification power in a range between 3.3 and 4.8. It is also possible to adopt an optical system having a zooming function variable within a predetermined range.

Second Embodiment

Next, a method to use an angular velocity sensor for obtaining the downward wearing angle will be described as another embodiment. For example, a gyro sensor may be adopted as the angular velocity sensor and is attached to the frame 1. Here, when an operator wearing the frame 1 takes a working posture, the gyro sensor outputs voltage corresponding to an inclination angle of the frame 1. The computer 20 calculates the downward wearing angle by performing arithmetic processing on a value of the output signal from the gyro sensor. In this case, the downward wearing angle obtained through the arithmetic processing is commonly used for the right and left. Here, owing to using the angular velocity sensor, the distance A and distance B are not required to be measured.

Then, opening portions are formed at the right and left carrier lenses 5 based on the right pupil position, the left pupil position, and the inward wearing angles p, q which are obtained with the same method as in the first embodiment. Subsequently, the loupe units 2 are inserted and fixed thereto.

The present invention providing a binocular loupe which is used during medical surgery or precision machine operation relates to a method for manufacturing a binocular loupe which fits to pupil positions of both eyes and a working posture in accordance with physicality of each individual operator. Thus, the present invention has industrial applicability.

What is claimed is:

1. A method for manufacturing a binocular loupe in which loupe units are attached to carrier lenses mounted on a frame selected in accordance with an operator, comprising steps of:
   (a) radiating strobe light from a below-located operational manipulating position in a state that the operator wearing the frame on which the carrier lenses are mounted stares the operational manipulating position in a working posture to use the binocular loupe;
   (b) photographing reflection light of the strobe light reflected from pupils of the operator with a first imaging device which is arranged at the operational manipulating position;
   (c) obtaining side posture image data of the operator in the working posture with a second imaging device which is arranged at either or both of the right and left sides of the operator at a position or positions being apart therefrom by a predetermined distance;
   (d) electrically specifying a right pupil position (X1, Y1) and a left pupil position (X2, Y2) of the operator from a center point of the frame based on front image data obtained by the first imaging device;
   (e) measuring, from the side posture image data, a distance A from the operational manipulating position to the carrier lenses and a horizontal distance B from the operational manipulating position to a vertical line passing through the carrier lens in a direction perpendicular thereto, and determining downward wearing angles r1, r2 of the loupe units which are to be attached to the right and left carrier lenses based on the measured distance A and distance B;
   (f) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position; and
   (g) forming opening portions at the right and left carrier lenses based on the right pupil position, the left pupil position, the downward wearing angles r1, r2, and the inward wearing angles p, q, and inserting and fixing the right and left loupe units to the opening portions.

2. The method for manufacturing a binocular loupe according to claim 1, wherein the carrier lenses are eyesight correcting lenses for the operator.

3. The method for manufacturing a binocular loupe according to claim 2,
   wherein, the operator being in a standing posture as looking into distance above the operational manipulating position after releasing the working posture, the carrier lenses are manufactured with steps of:
   radiating strobe light from the operational manipulating position in a state that the operator wearing the frame on which the carrier lenses are mounted uses the binocular loupe in the standing posture;
   photographing reflection light of the strobe light reflected from pupils of the operator with the first imaging device which is arranged at the operational manipulating position;
   electrically specifying a right pupil position (X3, Y3) and a left pupil position (X4, Y4) of the operator from a center point of the frame based on front image data obtained by the first imaging device; and
   arranging centers of the eyesight correcting lenses at the right pupil position (X3, Y3) and the left pupil position (X4, Y4) of the operator.

4. The method for manufacturing a binocular loupe according to claim 1, wherein the loupe units have fixed magnification power to provide enlarged view of the operational manipulating position or a zooming function with variable magnification power within a predetermined range.

5. The method for manufacturing a binocular loupe according to claim 1,
   wherein the first imaging device is a digital camera which includes a strobe light radiation device and electrically stores image data in memory.

6. The method for manufacturing a binocular loupe according to claim 1, wherein the side posture image data of the operator is obtained in the step (c) at timing as being synchronized with the strobe light radiating in the step (a).

7. The method for manufacturing a binocular loupe according to claim 1, wherein the step of electronically specifying the right pupil position (X1, Y1) and the left pupil position (X2, Y2) of the operator in the step (d) is performed by determining center points of segments, in predetermined sections of the front image data at right and left sides from the center point of the frame, which have area respectively in a predetermined range with luminance exceeding a predetermined threshold and have luminance respectively being more than a predetermined number of times as high as in a periphery section thereof.

8. The method for manufacturing a binocular loupe according to claim 1,
wherein the second imaging device is a digital camera which electrically stores image data of the side posture of the operator in memory, and
the distance A from the operational manipulating position to the carrier lenses and the horizontal distance B from the operational manipulating position to the vertical line passing through the carrier lens in the direction perpendicular thereto measured in the step (e) are calculated based on imaging magnification power of the second imaging device and a distance against the operator.

9. The method for manufacturing a binocular loupe according to claim 1, wherein the linear distances C, D from the right pupil position and the left pupil position of the operator to the operational manipulating position and the distance G from the center point of the frame to the operational manipulating position in the step (f) are measured with a non-contact ranging device which is arranged at the operational manipulating position.

10. The method for manufacturing a binocular loupe according to claim 9, wherein the linear distances C, D from the right pupil position and the left pupil position of the operator to the operational manipulating position and the distance G from the center point of the frame to the operational manipulating position in the step (f) are measured with laser measuring equipment.

11. The method for manufacturing a binocular loupe according to claim 9, wherein the linear distances C, D from the right pupil position and the left pupil position of the operator to the operational manipulating position and the distance G from the center point of the frame to the operational manipulating position in the step (f) are measured with a ranging sensor using infrared light.

12. The method for manufacturing a binocular loupe according to claim 9, wherein the linear distances C, D from the right pupil position and the left pupil position of the operator to the operational manipulating position and the distance G from the center point of the frame to the operational manipulating position in the step (f) are measured with a ranging sensor using ultrasonic waves.

13. The method for manufacturing a binocular loupe according to claim 1, wherein the determining of the downward wearing angles r1, r2 of the loupe units in the step (e) is performed based on the distance A from the operational manipulating position to the carrier lenses, the distance B from the operational manipulating position to the vertical line passing through the carrier lens in the horizontal direction as being perpendicular thereto, and a downward forward-leaning angle s of the frame.

14. The method for manufacturing a binocular loupe according to claim 1, wherein the inward wearing angles p, q in the step (f) are set to be smaller with increase of a corneal apex distance between a corneal of the operator and a back surface of the carrier lens.

15. The method for manufacturing a binocular loupe according to claim 1, wherein the forming of the opening portions for mounting the right and left loupe units in the step (g) is performed by cutting with an NC processing machine.

16. The method for manufacturing a binocular loupe according to claim 15, wherein the inserting and fixing of the right and left loupe units to the opening portions formed at the right and left carrier lenses in the step (g) are performed in a state that the right and left loupe units and the right and left carrier lenses are positioned with laser positioning equipment at the downward wearing angles r1, r2 and the inward wearing angles p, q.

17. A method for manufacturing a binocular loupe in which loupe units are attached to carrier lenses mounted on a frame selected in accordance with an operator, comprising steps of:
(a) radiating strobe light from a below-located operational manipulating position in a state that the operator wearing the frame on which the carrier lenses are mounted stares the operational manipulating position in a working posture to use the binocular loupe;
(b) photographing reflection light of the strobe light reflected from pupils of the operator with an imaging device which is arranged at the operational manipulating position;
(c) electrically specifying a right pupil position (X1, Y1) and a left pupil position (X2, Y2) of the operator from a center point of the frame based on front image data obtained by the imaging device;
(d) determining downward wearing angles r1, r2 of the loupe units which are to be attached to the carrier lenses based on output of an angular velocity sensor attached to the frame in the working posture;
(e) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position; and
(f) forming opening portions at the right and left carrier lenses based on the right pupil position, the left pupil position, the downward wearing angles r1, r2, and the inward wearing angles p, q, and inserting and fixing the right and left loupe units to the opening portions.

18. The method for manufacturing a binocular loupe according to claim 17, wherein the carrier lenses are eyesight correcting lenses for the operator.

19. The method for manufacturing a binocular loupe according to claim 18,
wherein, the operator being in a standing posture as looking into distance above the operational manipulating position after releasing the working posture, the carrier lenses are manufactured with steps of:
radiating strobe light from the operational manipulating position in a state that the operator wearing the frame on which the carrier lenses are mounted uses the binocular loupe in the standing posture;
photographing reflection light of the strobe light reflected from pupils of the operator with the imaging device which is arranged at the operational manipulating position;

electrically specifying a right pupil position (X3, Y3) and a left pupil position (X4, Y4) of the operator from a center point of the frame based on front image data obtained by the imaging device; and arranging centers of the eyesight correcting lenses at the right pupil position (X3, Y3) and the left pupil position (X4, Y4) of the operator.

20. The method for manufacturing a binocular loupe according to claim 17, wherein the loupe units have fixed magnification power to provide enlarged view of the operational manipulating position or a zooming function with variable magnification power within a predetermined range.

21. The method for manufacturing a binocular loupe according to claim 17,
wherein the imaging device is a digital camera which includes a strobe light radiation device and electrically stores image data in memory.

22. The method for manufacturing a binocular loupe according to claim 17, wherein the step of electronically specifying the right pupil position (X1, Y1) and the left pupil position (X2, Y2) of the operator in the step (c) is performed by determining center points of segments, in predetermined sections of the front image data at right and left sides from the center point of the frame, which have area respectively in a predetermined range with luminance exceeding a predetermined threshold and have luminance respectively being more than a predetermined number of times as high as in a periphery section thereof.

23. The method for manufacturing a binocular loupe according to claim 17, wherein the linear distances C, D from the right pupil position and the left pupil position of the operator to the operational manipulating position and the distance G from the center point of the frame to the operational manipulating position in the step (e) are measured with a non-contact ranging device which is arranged at the operational manipulating position.

24. The method for manufacturing a binocular loupe according to claim 23, wherein the linear distances C, D from the right pupil position and the left pupil position of the operator to the operational manipulating position and the distance G from the center point of the frame to the operational manipulating position in the step (e) are measured with a ranging sensor using infrared light.

25. The method for manufacturing a binocular loupe according to claim 23, wherein the linear distances C, D from the right pupil position and the left pupil position of the operator to the operational manipulating position and the distance G from the center point of the frame to the operational manipulating position in the step (e) are measured with a ranging sensor using ultrasonic waves.

26. The method for manufacturing a binocular loupe according to claim 17, wherein the linear distances C, D from the right pupil position and the left pupil position of the operator to the operational manipulating position and the distance G from the center point of the frame to the operational manipulating position in the step (e) are measured with laser measuring equipment.

27. The method for manufacturing a binocular loupe according to claim 17, wherein the inward wearing angles p, q in the step (e) are set to be smaller with increase of a corneal apex distance between a corneal of the operator and a back surface of the carrier lens.

28. The method for manufacturing a binocular loupe according to claim 17, wherein the forming of the opening portions for mounting the right and left loupe units in the step (f) is performed by cutting with an NC processing machine.

29. The method for manufacturing a binocular loupe according to claim 28, wherein the inserting and fixing of the right and left loupe units to the opening portions formed at the right and left carrier lenses in the step (f) are performed in a state that the right and left loupe units and the right and left carrier lenses are positioned with laser positioning equipment at the downward wearing angles r1, r2 and the inward wearing angles p, q.

30. A method for manufacturing a binocular loupe in which loupe units are attached to carrier lenses mounted on a frame selected in accordance with an operator, comprising steps of:
(a) radiating strobe light from a below-located operational manipulating position in a state that the operator wearing the frame on which the carrier lenses are mounted stares the operational manipulating position in a working posture to use the binocular loupe;
(b) photographing reflection light of the strobe light reflected from pupils of the operator with a first imaging device which is arranged at the operational manipulating position;
(c) obtaining side posture image data of the operator in the working posture with a second imaging device which is arranged at either or both of the right and left sides of the operator at a position or positions being apart therefrom by a predetermined distance;
(d) electrically specifying a right pupil position (X1, Y1) and a left pupil position (X2, Y2) of the operator from a center point of the frame based on front image data obtained by the first imaging device;
(e) measuring a distance A from the operational manipulating position to the carrier lenses in the working posture with a ranging sensor which is attached to the frame, measuring, from the side posture image data, a horizontal distance B from the operational manipulating position to a vertical line passing through the carrier lens in a direction perpendicular thereto, and determining downward wearing angles r1, r2 of the loupe units which are to be attached to the right and left carrier lenses based on the measured distance A and distance B;
(f) determining inward wearing angles p, q of the loupe units which are to be attached to the right and left carrier lenses based on linear distance C, D from the right pupil position and the left pupil position of the operator to the operational manipulating position and a distance G from the center point of the frame to the operational manipulating position; and
(g) forming opening portions at the right and left carrier lenses based on the right pupil position, the left pupil position, the downward wearing angles r1, r2, and the inward wearing angles p, q, and inserting and fixing the right and left loupe units to the opening portions.

* * * * *